United States Patent [19]

Helfgott et al.

[11] Patent Number: 4,530,356

[45] Date of Patent: Jul. 23, 1985

[54] OPHTHALMIC SURGICAL INSTRUMENT WITH BEVELED TIP

[76] Inventors: Maxwell A. Helfgott, 5640 Bradley Blvd., Bethesda, Md. 20814; Gerald N. Helfgott, 5513 Uppingham St., Chevy Chase, Md. 20815

[21] Appl. No.: 464,896

[22] Filed: Feb. 8, 1983

[51] Int. Cl.³ .............................................. A61B 17/32
[52] U.S. Cl. ................................................... 128/305
[58] Field of Search ..................... 128/305, 751–755; 604/22; 30/208, 241

[56] References Cited

U.S. PATENT DOCUMENTS

| | | |
|---|---|---|
| 737,293 | 8/1903 | Summerfeldt . |
| 1,585,934 | 5/1926 | Muir . |
| 1,663,761 | 3/1928 | Johnson . |
| 1,837,503 | 12/1931 | Thostenson . |
| 2,850,007 | 9/1958 | Lingley . |
| 3,001,522 | 9/1961 | Silverman . |
| 3,007,471 | 11/1961 | McClure, Jr. . |
| 3,589,363 | 6/1971 | Banko et al. . |
| 3,606,878 | 9/1971 | Kellogg, Jr. . |
| 3,693,613 | 9/1972 | Kelman . |
| 3,734,099 | 5/1973 | Bender et al. . |
| 3,776,238 | 12/1973 | Peyman et al. . |
| 3,805,787 | 4/1974 | Banko . |
| 3,815,604 | 6/1974 | O'Malley et al. . |
| 3,844,272 | 10/1974 | Banko . |
| 3,882,872 | 5/1975 | Douvas et al. .............. 128/305 |
| 3,884,237 | 5/1975 | O'Malley et al. . |
| 3,884,238 | 5/1975 | O'Malley et al. . |
| 3,961,621 | 6/1976 | Northeved . |
| 3,994,297 | 11/1976 | Kopf . |
| 4,011,869 | 3/1977 | Seiler, Jr. . |
| 4,099,529 | 7/1978 | Peyman . |
| 4,108,182 | 8/1978 | Hartman et al. . |
| 4,111,207 | 9/1978 | Seiler, Jr. . |
| 4,167,944 | 9/1979 | Banko . |
| 4,200,106 | 4/1980 | Douvas et al. . |
| 4,210,146 | 7/1980 | Banko . |
| 4,316,465 | 2/1982 | Dotson, Jr. . |

FOREIGN PATENT DOCUMENTS 2848314 5/1979 Fed. Rep. of Germany .
400319 2/1974 U.S.S.R. .
728852 5/1980 U.S.S.R. .

OTHER PUBLICATIONS

G. A. Peyman et al., "Experimental Vitrectomy, New Technical Aspects", *American Journal of Ophthalmology*, vol. 75, No. 5, pp. 774–778 (May 1973).

R. G. Michels et al., "Vitreous Surgery: History and Current Concepts", *Ophthalmic Surgery*, vol. 5, No. 4, pp. 13–59.

N. G. Douvas, "The Cataract Roto-Extractor (A Preliminary Report)", *Transactions of the American Academy of Ophthalmology and Otolaryngology*, vol. 77, pp. 792–800, (Nov.–Dec. 1973).

G. A. Peyman and N. A. Dodich, "Experimental Vitrectomy: Instrumentation and Surgical Technique", *Arch. Ophthal.*, vol. 86, pp. 548–551 (Nov. 1971).

H. G. Scheie, "Aspiration of Congenital or Soft Cataracts: A New Technique", *American Journal of Ophthalmology*, vol. 50, pp. 1048–1056 (1960).

R. Machemer et al., "Vitrectomy: A Pars Plana Approach", *Transactions of the American Academy of Ophthalmology and Otolaryngology*, vol. 75, pp. 813–820 (Jul.–Aug. 1971).

*Primary Examiner*—Michael H. Thaler
*Attorney, Agent, or Firm*—Robbins & Laramie

[57] ABSTRACT

A surgical instrument for ophthalmic use comprises a rigid outer tubular member and a rigid inner tubular member which is axially slidable within the outer tubular member. The outer tubular member has a closed distal end which is beveled at an oblique angle with respect to the longitudinal axis of the outer tubular member. The outer tubular member is also provided with a distal side wall opening, serving as a cutting port, which occupies at least part of the area covered by the distal beveled portion of the outer tubular member. The inner tubular member has an open and tapered distal end terminating in a cutting edge which is movable into the beveled end of the outer tubular member in order to sever material drawn into the cutting port. The instrument is useful for cutting near the retina since the cutting port is located very close to the instrument tip, and is also advantageous in that the beveled tip can be used to elevate or dissect intraocular material prior to cutting. Premature blade wear is avoided by providing a counter-bevel on the cutting portion of the inner tubular member in order to provide a spacing between the cutting edge and the interior edge of the cutting port. Also disclosed is a method for making the instrument in which an oblique cut is formed through the inner and outer tubular members at the same time.

19 Claims, 17 Drawing Figures

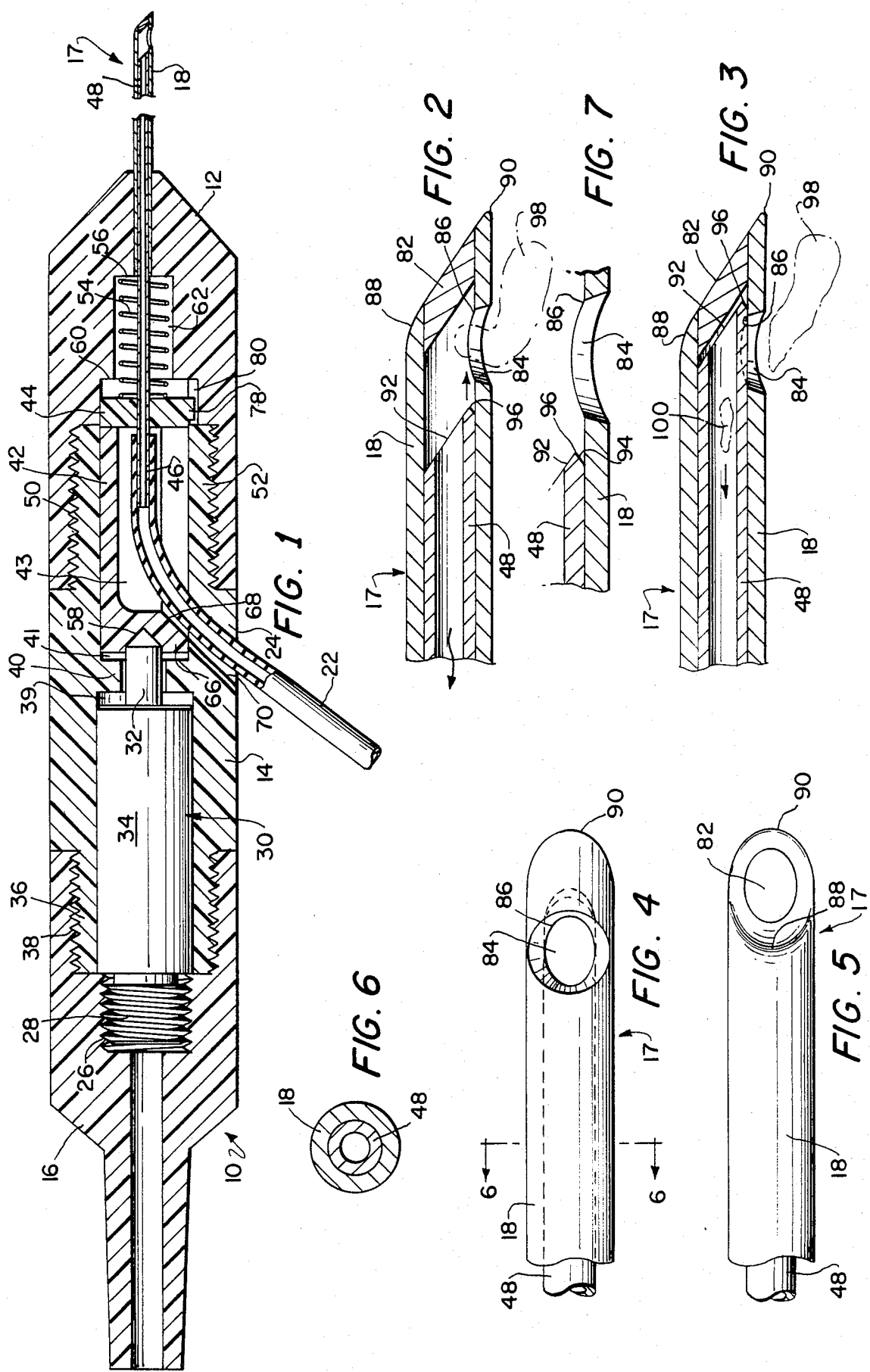

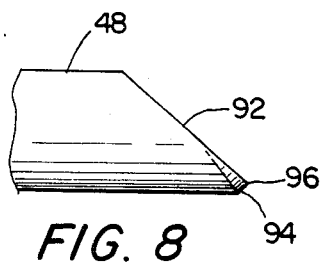
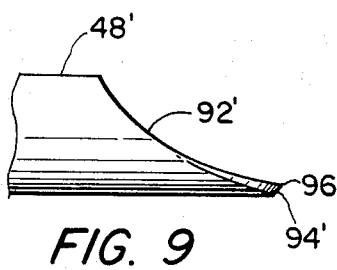
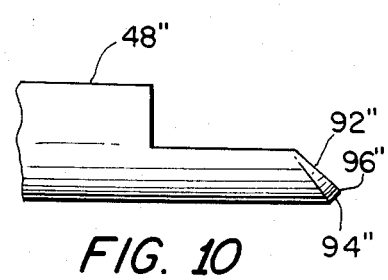
FIG. 8  FIG. 9  FIG. 10
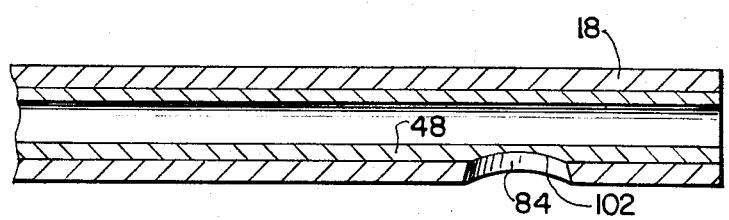
FIG. 11
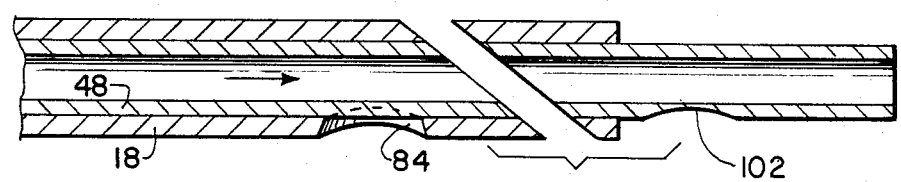
FIG. 12
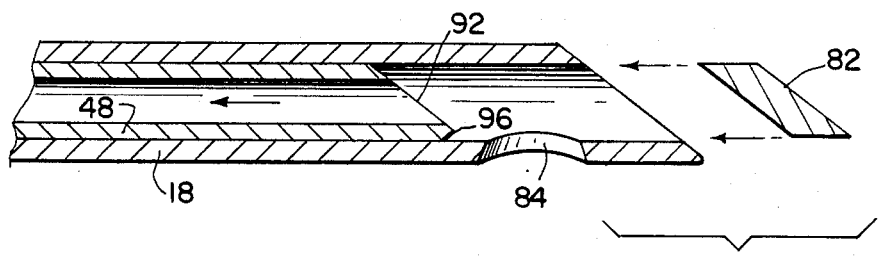
FIG. 13
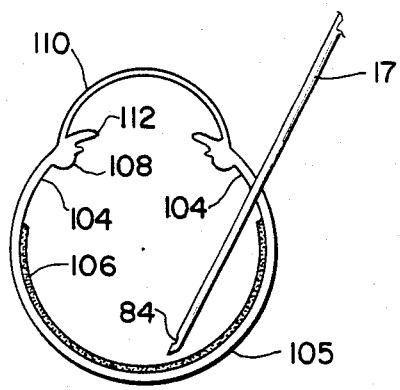
FIG. 14

OPHTHALMIC SURGICAL INSTRUMENT WITH BEVELED TIP

BACKGROUND OF THE INVENTION

1. Field of the Invention

The present invention relates generally to surgical instruments, and is particularly concerned with an ophthalmic surgical instrument having an asymmetrically tapered or beveled tip and a method for making said instrument.

2. Description of the Prior Art

Endophthalmic surgery, or surgery on an intact and normally pressurized eye, represents an important and relatively recent development in the field of ophthalmology. In this technique, the existing optical pathways of the pressurized ocular globe are utilized for visualization during delicate intraocular manipulations. Maintenance of positive intraocular pressure tends to preserve and stabilize the spatial relationships among the various intraocular tissues.

The archetypal endophthalmic procedure is the cataract aspiration technique of extracapsular cataract surgery described by Scheie, *Am. J. Ophthal.* 50:1048 (1960), wherein an instrument is passed through a small incision at the margin of the cornea into the anterior aqueous chamber of the eye to incise the anterior capsular membrane of the lens. The aqueous, which leaks out during this manipulation, is replaced by a gravity-fed infusion of physiologic saline through a cannula inserted into the anterior chamber through a second small incision. A blunt needle is then inserted through the first incision into the lens, whereupon gentle suction aspirates the soft lens substance leaving the posterior capsular membrane in place. Whatever volume is removed or leaks from the two small incisions is replaced by the continuous gravity feed of saline. Absent any seepage or applied suction, the pressure in the eye stabilizes at a point determined by the physical elevation of the saline column above the level of the eye. At the end of the procedure, all tubes are withdrawn and the incisions are sutured.

Conceptually, all modern endophthalmic procedures are variations and refinements of the foregoing technique. In pars plana vitrectomy, for example, an incision is made through the scleral coat of the eye in the pars plana region between the iris and the anteriormost retina. A tract is cut with a long, sharp knife into the vitreous, and the tip of the vitrectomy instrument is placed in the eye. Infusion is provided through a separate incision or through cannula concentric with the vitrectomy instrument itself. Gentle aspiration provided through the tip of the vitrectomy instrument engages vitreous or other intraocular tissues, which are then sheared or sliced in small bits and removed from the eye through an aspiration tube. Illumination is provided by optical fibers which may be concentric with the vitrectomy instrument or inserted separately. The procedure is visualized through the dilated pupil with a high magnification operating microscope. Actuation of the various functions at the instrument tip is usually by remote foot control.

The earliest powered vitrectomy instruments utilized rotary cutting elements. See, e.g., Machemer et al., *Trans. Am. Acad. Ophthal. Otolaryng.* 75:813 (1971). Rotary instruments, however, tended to cause undesirable tangential pulling or shearing of the tissue being severed, particularly when the rotary cutting element became dull. This sometimes resulted in partial wrapping or spooling of the uncut tissue around the rotating cutting element. Efforts to avoid these effects led to the development of linearly reciprocating cutting instruments, an early example of which is described by Peyman et al., *Arch. Ophthal.* 86:548 (1971). The instrument portion of the Peyman et al. handpiece consists of two concentric tubes with a hole near the distal end of the outer tube. Cutting is performed by the chopping action of the sharpened end of the inner tube against the plane interior end of the outer tube. Suction applied to the inner tube urges the tissue to be severed into the hole in the outer tube and then removes the severed bits of tissue from the eye. Infusion is provided through a small tube running parallel to the outer concentric tube. The necessary powered reciprocation of the inner tube relative to the fixed outer tube is provided by a small electrical solenoid, the oscillation rate of which can be varied. A description of this handpiece can also be found in U.S. Pat. No. 3,776,238, to Peyman et al.

More recently, pneumatic devices have replaced electrical solenoids as the source of linear reciprocating motion for the inner tube of the cutting instrument. This development is reflected, for example, in Peyman et al., *Am. J. Ophthal.* 75:774 (1973), and in U.S. Pat. Nos. 3,815,604, 3,884,237 and 3,884,238, all to O'Malley et al. Pneumatic devices are readily adaptable to linear reciprocating motion, do not inherently generate heat, and can be constructed from lightweight materials. Additional advantages of pneumatic power sources are a more evenly modulated power pulse and elimination of the potential electrical hazard presented by electrical solenoid devices.

Another relatively recent development, also reflected in the previously-cited U.S. patents to O'Malley et al., is the substitution of a shear-type cutting instrument for the earlier chopping cutter disclosed by Peyman et al. In the shear-type cutter, the cutting action takes place between the sharpened distal edge of the inner tube and the sharpened edge of a hole or port formed near the distal end of the outer tube. The shear-type cutter produces less wear on the sharpened edge of the inner tube than is the case with the chopping cutter, and is the type of cutter which is used most frequently at the present time.

Many of the problems experienced with the early vitrectomy instruments were related to the use of bulky combination probes, which often required concentric infusion, cutting and illumination instruments to be inserted into the vitreous body through a single scleral incision. Typically, the scleral incision is linear and has a length approximately equal to one-half the circumference of the instrument probe, in order to achieve a fluid-tight fit. The instrument tip is introduced with a twisting motion; often this is preceded by the insertion of a beveled hypodermic needle of the same diameter as the probe. The concentric fiber-optic illumination or infusion sleeves with sharp "shoulders" would occasionally catch on the elastic choroidal layer or adherent vitreous base, causing choroidal separation or retinal tears. These problems have been minimized by miniaturization, streamlining, and specialization of the intraocular probes. For example, it is common at the present time to insert the infusion cannula and illumination fiber into the vitreous body through one or more separate scleral incisions, rather than by attaching these devices to the vitrectomy instrument probe.

Improved instrumentation has led to more intricate and complex manipulation near, on, and beneath the retinal surface. One of the basic rules of endophthalmic surgery within the vitreous is that the distal cutting or aspiration port must always be visible, so that the surgeon can insure that only material which is intended to be cut enters the port. The ability to cut close to the retinal surface with constant visualization of the cutting port is a highly desirable feature of vitrectomy tip design. This advantage is realized when the cutting port is located as close as possible to the instrument tip, and when the configuration of the instrument tip is such that the port can be positioned as close as possible to the retinal surface while still remaining within the surgeon's line of sight.

For the most part, the vitrectomy instruments which are available at the present time have two different types of tip configurations. The first type, exemplified by U.S. Pat. No. 3,994,297, to Kopf, and U.S. Pat. No. 4,011,869, to Seiler, Jr., is characterized by a symmetrically rounded tip shape which is essentially hemispherical. Similar tip shapes can be found in the above-mentioned U.S. Pat. Nos. 3,815,604, 3,884,237 and 3,884,238, all to O'Malley et al. Although this type of tip shape facilitates penetration of the eye through the scleral incision, it suffers from the disadvantage that the cutting port in the outer tube must be located relatively far back from the instrument tip. The reason for this is that the vertically cut distal end of the inner cutting tube cannot be accommodated in the area of reduced cross-section defined by the rounded distal end of the outer tube. As a result, the forward stroke of the inner tube must terminate before the point where the outer tube begins to taper. The second type of tip configuration, exemplified by U.S. Pat. No. 4,099,529, to Peyman, and U.S. Pat. No. 4,111,207, to Seiler, Jr., is characterized by a flat tip shape which is formed essentially by closing off the distal end of the outer tube with a plane vertical wall. This arrangement allows the cutting port to be located relatively close to the instrument tip, but only at the expense of a blunt instrument tip which does not readily penetrate the eye.

In U.S. Pat. No. 4,210,146, to Banko, a surgical instrument is disclosed in which the inner cutting member consists of a flexible blade carried by an axially reciprocating drive shaft. As the shaft moves forward, the flexure of the blade allows it to move into the symmetrically rounded and tapered instrument tip, where the cutting port is located. This arrangement allows the cutting port to be located somewhat closer to the instrument tip than would be possible with a rigid inner cutting tube, although this advantage is offset by the need to substitute a precisely machined flexible blade and drive shaft arrangement for the simple rigid tube that is conventionally used as the inner cutting member.

Another basic technique in endophthalmic surgery is the use of spatulated instruments or picks to elevate or dissect periretinal and epiretinal membranes prior to excising them. The round or blunt tips of most currently available vitrectomy instruments are not particularly useful for these maneuvers. For this reason, it is common to employ a separate instrument, such as a hooked needle, to elevate the membrane to a point where it can be engaged and excised with the vitrectomy instrument tip. A vitrectomy instrument with a beveled tip would be more desirable in this situation, since the sharp distal edge at the end of the beveled tip might allow the instrument itself to be used as a spatula for elevating or dissecting intraocular material prior to cutting. The only known example of a vitrectomy instrument with a beveled tip is that shown by Peyman et al., *Am. J. Ophthal.* 75:774 (1974), at FIG. 5D, although the taper angle of this particular instrument tip is somewhat steeper than would be desired for convenient manipulation of the intraocular material to be excised. Also, in view of the rather substantial spacing between the cutting port and the distal end of the outer tube, the Peyman et al. instrument tip would not provide the advantage referred to earlier, that is, the ability to sever intraocular material positioned on or very close to the surface of the retina. Peyman et al. have reported other difficulties with this tip design, in particular, a limited blade life and a gradual enlargement of the spacing between the inner cutting tip and the outer tube to a point where cutting of the fiber vitreous bands became difficult or impossible.

SUMMARY OF THE INVENTION

In accordance with the present invention, the foregoing disadvantages and limitations of the prior art are substantially avoided by providing a vitrectomy instrument comprising rigid inner and outer tubular members, with the outer tubular member having a closed distal end which is beveled at an oblique angle with respect to the longitudinal axis of the outer tubular member. The inner tubular member is axially slidable within the outer tubular member and has an open and tapered distal end terminating in a cutting edge which is movable into the beveled end of the outer tubular member. The outer tubular member is provided with a distal side wall opening, serving as a cutting port, which occupies at least part of the area covered by the beveled portion of the outer tubular member. Preferably, the taper at the open distal end of the inner tubular member is formed by providing the distal end of the inner tubular member with a bevel similar to that of the outer tubular member, so that the distal ends of the inner and outer tubular members assume a nested relationship when the inner tubular member moves forward during a cutting stroke. Also, the distal edge surface of the inner tubular member which moves across the distal side wall opening in the outer tubular member is preferably counter-beveled in order to provide a sharpened cutting edge which is spaced away from the edge of the distal side opening lying along the inside surface of the outer tubular member.

The vitrectomy instrument of the present invention provides several important advantages over previously available instruments of this general type. Most importantly, the fact that the tapered distal end of the inner tubular member is movable into the beveled end of the outer tubular member, coupled with the fact that the cutting port is located at least partially within the area covered by the beveled portion of the outer tubular member, results in the cutting port being located as close as possible to the instrument tip. This is a desirable feature when the instrument is used for cutting close to the surface of the retina. Unlike previous instruments with flat or blunt tips, however, this result is achieved without sacrificing the sharpened or tapered aspect of the instrument tip, which facilitates penetration of the eye during initial insertion of the instrument. The beveled distal end of the outer tubular member is also advantageous in that it allows the instrument tip to be placed in an optimal position during near-retinal work, with the beveled surface lying along the retina and the cutting port positioned close to the retina and in a direct line of sight with the anterior part of the eye.

Another important advantage of the invention resides in the use of a counter-bevel to form the sharpened cutting edge at the distal end of the inner tubular member. As a result of the counter-bevel, the sharpened edge of the inner tubular member is spaced slightly away from the inside edge of the cutting port formed in the outer tubular member and is therefore not in danger of striking the edge of the port during a cutting stroke. This avoids premature dulling of the cutting edges and prolongs the useful life of the surgical instrument.

The vitrectomy instrument of the present invention lends itself readily to mass production methods, and it is to one such method that another aspect of the invention is directed. The inventive method utilizes an instrument blank comprising a rigid outer tube and a rigid inner tube coaxially and slidably arranged within the outer tube. The inner and outer tubes each have open distal and proximal ends. In carrying out the method, a hole is formed in the side wall of the outer tube at a point near its distal end. An oblique cut is then formed simultaneously through the inner and outer tubes at a point between the distal end of the outer tube and the hole previously formed in the side wall of the outer tube. The simultaneous cut assures that the inner and outer tubular members are cut at the same oblique angle with respect to their common longitudinal axis. The distal cut portions of the inner and outer tubes are then discarded. The distal end of the instrument is completed by permanently closing the oblique cut end of the outer tube, as for example by a plug weld, to provide a closed and beveled distal instrument tip. In order to allow the distal edge surface of the inner tube to be provided with the desired counter-bevel to form the sharpened cutting edge, the inner tube may be temporarily advanced so that its oblique cut distal end projects out of the oblique cut distal end of the outer tube, this being accomplished prior to closing off the distal end of the outer tube.

BRIEF DESCRIPTION OF THE DRAWINGS

The various objects, advantages and novel features of the present invention will be more readily apprehended from the following detailed description when read in connection with the appended drawings, in which:

FIG. 1 is a side sectional view of a powered surgical handpiece which is fitted with the vitrectomy instrument of the present invention;

FIGS. 2 and 3 are enlarged side sectional views of the vitrectomy instrument tip, illustrating the forward movement of the inner tube during a cutting stroke;

FIGS. 4 and 5 are enlarged bottom and plan views, respectively, of the vitrectomy instrument tip;

FIG. 6 is a sectional view of the instrument tip taken along the line 6—6 in FIG. 4, illustrating the coaxial relationship of the inner and outer tubes;

FIG. 7 is a detailed sectional view, further enlarged with respect to FIGS. 2-6, illustrating the configuration of the sharpened cutting edge formed on the distal end of the inner tube;

FIGS. 8-10 are side elevational views of three different types of tapered distal end configurations for the inner cutting tube;

FIGS. 11-13 are sequential side sectional views illustrating a preferred method for making the vitrectomy instrument;

FIG. 14 is a sectional view of the human eye illustrating the insertion of the vitrectomy instrument through the pars plana region;

Throughout the drawings, like reference numerals are used to identify like parts.

DETAILED DESCRIPTION OF THE PREFERRED EMBODIMENT

Figure 15:
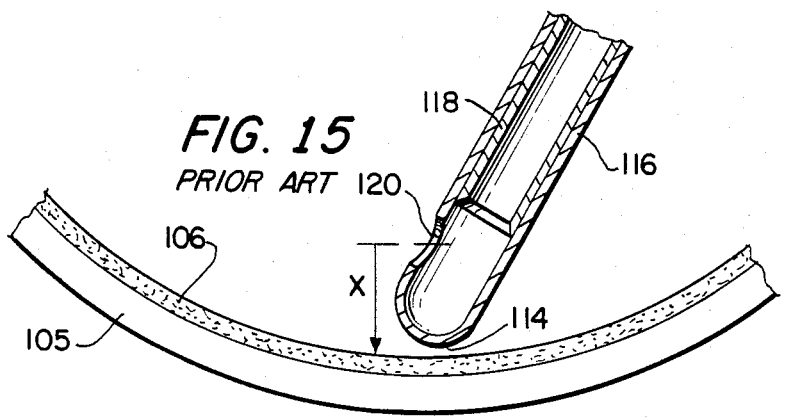
FIG. 15 is a detailed sectional view of the human eye, enlarged with respect to FIG. 14, illustrating a prior art vitrectomy instrument in position for cutting intraocular material near the retina.

FIG. 1 is a side sectional view of a powered surgical handpiece 10 which may be fitted with the vitrectomy instrument of the present invention. The handpiece 10 is described in detail in the applicants' earlier U.S. Pat. No. 4,314,560, which patent is expressly incorporated herein by reference.

The handpiece 10 will be seen to include a cylindrical housing comprising an anterior cylindrical section 12, a central cylindrical section 14, and a rear cylindrical section 16. The rear part central housing section 14 includes an externally threaded portion 36 which engages a corresponding internally threaded portion 38 of the rear housing section 16. In a similar manner, the forward end 52 of the central housing section 14 is externally threaded in order to engage a corresponding internally threaded portion 50 of the anterior housing section 12. The central section 14 and rear section 16 together comprise what may be referred to as the posterior section of the handpiece or, in connection with the components they receive, as the main body of the handpiece.

The anterior section 12 of the handpiece is fitted with a projecting tubular surgical instrument 17 which includes an elongated outer tubular member 18 and an elongated inner tubular member 48. The inner tubular member 48 is coaxially and slidably received within the outer tubular member 18 for axial reciprocation therein. The particular shape of the instrument 17 at its distal tip, as defined by the distal end configurations of the outer and inner tubular members 18 and 48, is the subject matter of the present invention and will be described in some detail hereinafter.

A flexible pneumatic supply line, not shown, is attached to the rear section 16 of the handpiece 10 and is connected at its opposite end to a suitable pneumatic power supply, also not shown, for providing intermittent pulses of compressed air or other gas to a pneumatic actuator 30 within the handpiece. The pneumatic actuator 30 imparts axial reciprocating motion to the inner tubular member 48 within the fixed outer tubular member 18, the latter being press-fitted into the anterior section 12 of the handpiece. A flexible tube 22 is connected at a point within the handpiece to the proximal end of the inner tubular member 48, as shown, and passes loosely out of the handpiece through an opening 24 formed in the cylindrical side surface of the handpiece. The inclined rear wall portion 70 of the opening 24 and the inclined guide surface 68 formed on the closed end portion 66 of a coupling member 42 cooperate to assist the flexible tube 22 in bending smoothly as it passes out of the handpiece. The flexible tube 22 will normally be used for applying suction (aspiration) to the inner tubular member 48 when the projecting surgical instrument 17 is of the type shown, although for other types of instruments the flexible tube 22 may be used to conduct a saline infusion into the inner tubular member. In this connection, it should be noted that the anterior portion 12 of the handpiece is removable to permit the attachment of different types of surgical instruments, a capability which will become more apparent as the description proceeds.

With continued reference to FIG. 1, the coupled rear section 16 and central section 14 of the handpiece housing together define an internal cylindrical cavity 39 for receiving the pneumatic actuator 30. The rear section 16 of the housing is provided with internal threads 26 for making airtight engagement with a threaded fitting 28 formed on the rear part of the pneumatic actuator 30. The pneumatic actuator 30 contains an internal piston and spring return for urging a pusher member 32 linearly or axially outward with respect to the cylindrical body portion 34 of the actuator in response to the intermittent pneumatic pressure pulses supplied through the fitting 28. An annular wall 40 located a short distance behind the opening 24 in the central housing section 14 defines the forward extent of the cavity 39 and provides a circular aperture through which the pusher member 32 passes. The conical tip of the pusher member 32 is received in a correspondingly shaped depression 58 formed in one end of the coupling member 42.

The coupling member 42 is slidably received in a cylindrical cavity 41 located forward of the annular wall 40 and serves to transmit the axial reciprocating motion of the pusher member 32 to a disk-shaped platform member 44. The platform member 44 is secured to the inner tubular member 48 of the surgical instrument at a point somewhat ahead of the proximal end of the inner tube 48, thereby insuring sufficient room for the attachment of the flexible tube 22 to the inner tube 48. The platform member 44 is maintained in abutting contact with the forward part of the coupling member 42 by virtue of a return spring 54. The return spring 54 is confined within a narrow cylindrical cavity 62 formed within the anterior section 12 of the handpiece, and is maintained in a compressed condition between the platform member 44 and the forward interior wall 56 of the cavity 62.

In operation, the coupling member 42 provides an abutting mechanical connection between the reciprocating pusher member 32 of the pneumatic actuator 30 and the platform member 44 which is secured to the proximal end 46 of the inner tubular member 48. At the same time, the recessed configuration of the coupling member 42 resulting from the open cavity 43 formed therein permits the flexible tube 22 to be connected to the proximal end 46 of the inner tubular member 48 as the latter reciprocates. Such reciprocation will occur when a positive pressure pulse is applied to the pneumatic actuator 30, causing the pusher member 32 to move forward. This forward motion is transmitted by the coupling member 42 to the platform member 44, which moves forward to the limit of its travel as defined by the annular shoulder 60. The forward motion of the platform member 44 causes an equal forward movement of the inner tubular member 48 within the outer tubular member 18, which produces a cutting stroke at the instrument tip as will be described hereinafter. When the pressure pulse terminates, the pusher member 32 retracts and the return spring 54 causes the platform member 44 and coupling member 42 to return to their rest positions. This motion retracts the inner tubular member 48 and completes the cycle of operation. The platform member 44 is provided with a projecting key 78 for engaging a corresponding longitudinal groove 80 formed on the interior surface of the anterior housing section 12. The purpose of this arrangement is to maintain the inner tubular member 48 in a fixed rotational position with respect to the outer tubular member 18.

The handpiece 10 of FIG. 1 allows interchangeability among different surgical instruments simply by uncoupling the anterior housing section 12 from the main body of the handpiece. This allows the removal of the inner and outer tubular members 48 and 18 which form the surgical instrument 17, together with the return spring 54, the platform member 44, and the anterior housing section 12 which carries all of these components. Such removal is readily accomplished in view of the fact that there is no necessity for rigid mechanical connection between the coupling member 42 and the platform member 44 when the handpiece is in its assembled condition, since the return spring 54 maintains these components in abutting contact with each other. When the anterior housing section 12 is removed, the platform member 44 and the coupling member 42 are separated, with the coupling member 42 remaining behind as part of the main body of the handpiece. A new anterior housing section, carrying a different type of surgical instrument (or the same type of instrument in cases where the previous instrument has simply become worn), as well as a new platform member and return spring, can now be coupled to the main body of the handpiece. The necessity of threading the flexible tube 22 through the opening 24 in the side of the handpiece during the substitution of a new instrument can be avoided by extending the opening 24 to the forward edge of the central housing section 14 to form an open-ended slot. When the anterior housing section 12 has been attached, its rear edge closes off the open end of the slot to form the functional equivalent of the opening 24.

The distal tip portion of the surgical instrument 17 is illustrated in more detail in the enlarged views of FIGS. 2-7. The surgical instrument 17 comprises, in general, an elongated outer tubular member 18 and an elongated inner tubular member 48, the latter being coaxially and slidably received within the outer tubular member 18. The inner tubular member 48 undergoes axial reciprocation within the outer tubular member 18 in the forward and reverse directions during operation of the handpiece 10 of FIG. 1 as described previously. The inner and outer tubular members 48 and 18 are each circular in cross section, as illustrated in FIG. 6, and are made of a rigid material, such as stainless steel. In practice, the inner and outer tubular members 18 and 48 may comprise lengths of stainless steel hypodermic tubing, appropriately machined and finished at their distal ends to provide the desired tip configuration, with the gauge of the inner tube selected to provide a smooth sliding fit within the outer tube 18.

With particular reference to FIGS. 2 and 3, the outer tubular member 18 will be seen to have its distal end beveled at an oblique angle with respect to the longitudinal axis of the outer tubular member. The oblique angle is preferably about 45° in the preferred embodiment, although different bevel angles can be employed if desired. The outer tubular member 18 is closed off at its distal end by an inclined end wall 82 which is joined to the inner side walls of the outer tubular member and flush-fitted with respect to the beveled end portion thereof. As will be described shortly, the inclined end wall 82 may consist of an elliptical disk or plug which is inserted into the oblique cut end of the outer tubular member 18 and is then welded or otherwise secured in place. The edge of the outer tubular member 18 above the inclined end wall 82 is preferably rounded, as indicated at 88, so as to merge smoothly with the outer plane face of the wall 82. This provides the upper beveled portion of the instrument tip with a smooth and rounded contour which facilitates placement of the instrument tip near the retina. The lower straight portion of the instrument tip terminates in an edge 90 which is either left sharp or is rounded only slightly, as shown, to allow the instrument tip to be used for elevating and dissecting intraocular material as will be described hereinafter.

The inner tubular member 48 is open at its distal end and is tapered in a manner which permits it to move into the beveled end portion of the outer tubular member 18 during a cutting stroke, as illustrated in FIG. 3. In the illustrated embodiment, the taper is provided by beveling the distal end 92 of the inner tubular member at an oblique angle with respect to the longitudinal axis of the inner tubular member, similar to the beveled distal end of the outer tubular member. Preferably, but not necessarily, the oblique angle defined between the beveled end of the inner tubular member and the longitudinal axis of the inner tubular member is substantially equal to the oblique angle defined between the beveled end of the outer tubular member and the longitudinal axis of the outer tubular member. In the preferred embodiment, this angle is about 45°. Equality between the two bevel angles will result in maximum nesting of the distal end of the inner tubular movement 48 within the beveled end of the outer tubular member 18 as the inner tubular member 48 moves forward during the cutting stroke, as will be apparent from FIG. 3.

As best see in FIGS. 2-4, the outer tubular member 18 is provided with a side opening 84 located in close proximity to its distal end. The opening 84 serves as a cutting port to allow intraocular material to be drawn into the instrument tip in response to suction applied at the proximal end of the inner tubular member 48. In accordance with an important aspect of the present invention, the cutting port 84 occupies at least part of the side wall area of the outer tubular member 18 that is covered by the inclined end wall 82. In other words, a horizontal projection of the inner surface of the inclined end wall 82, onto the interior side wall of the outer tubular member 18, includes at least a portion of the area occupied by the cutting port 84. When this condition is satisfied, as it is in the illustrated embodiment, it follows that the cutting port 84 is advantageously located at a position very close to the distal-most tip of the instrument 17, which in the present case would correspond to the distal edge 90. Such positioning of the cutting port 84 is highly desirable in cases where the intraocular material to be cut is located on or very near the retinal surface, as will be explained further in connection with FIGS. 15-17.

In practice, the surgical instrument 17 of FIGS. 2-7 may be fabricated by using surgical-quality stainless steel hypodermic tubing for the inner and outer tubular members 48 and 18. The outer tubular member 18 may comprise 20-gauge T-304 stainless steel with a wall thickness of 0.006 inch. The inner tubular member 48 may comprise 23.5-gauge tubing of the same material with a 0.003-inch wall thickness. The inclined end wall 82 may comprise a plug weld, preferably about 0.015 inch thick, which is flush-fitted into the oblique cut end of the outer tubular member 18. A metal such as stainless steel is the preferred material for the inclined end wall 82, since this allows the end wall 82 to be securely joined to the interior walls of the outer tubular member 18 by welding techniques. However, the end wall 82 can alternatively be made of a suitable plastic material if desired. The cutting port 84 has a slightly ovoid shape, as can be seen by comparing FIGS. 2 and 4, and is preferably hollowground with a fine cylindrical abrasive wheel to create the desired configuration. The grinding process gives rise to a sharpened cutting edge 86 which lies along the inside surface of the outer tubular member 18. The cutting edge 86 may be formed completely around the interior edge of the cutting port 84, as shown, and in fact this will automatically result when the port 84 is hollow ground with a cylindrical abrasive wheel. In operation, however, cutting of the intraocular material occurs principally between the cutting edge 96 on the distal end 92 of the inner tubular member 48 and the distal interior edge of the side opening 84, and for this reason the sharpened edge 86 may be confined to the forward or distal part of the cutting port 84 if desired. As illustrated in FIG. 4, the cutting port 84 defines an elliptical opening at the inner surface of the outer tubular member 18, with the major axis of the ellipse oriented parallel to the longitudinal axis of the outer tubular member. The diameter of the cutting port as measured in this direction is about 0.30 mm. The total distance moved by the inner tubular member 48 during the cutting stroke, that is, between the positions illustrated in FIGS. 2 and 3, is preferably between about 0.35 mm. and 0.40 mm. The clearance between the distal end 92 of the inner tubular member 48 and the plane inner surface of the inclined end wall 82 is on the order of 0.02 mm. when the inner tubular member 48 is in its forwardmost position as shown in FIG. 3. It should be understood that the foregoing dimensions and specifications, together with any dimensions and specifications given hereinafter, are presented merely by way of example and are not intended to limit the scope of the invention in any way except as defined in the appended claims.

The configuration of the cutting edge 96 formed at the distal end 92 of the inner tubular member 48 is also an important feature of the present invention, and is illustrated in detail in the enlarged view of FIG. 7. In this view it can be seen that the lower distal edge of the outer tubular member, which aligns with the cutting port 84, is provided with a counter-bevel 94. The counter-bevel 94 preferably forms an angle of about 45° with respect to the longitudinal axis of the inner tubular member 48, although it is inclined in the opposite sense relative to the 45° beveled distal end of the inner tubular member as a whole. Therefore, a cutting edge 96 subtending about 90°, defined at the intersection of the upper bevel 92 and the counter-bevel 94, is formed on the distalmost end of the inner tubular member 48. Due to the counter-bevel 94, the sharpened cutting edge 96 is spaced away from the interior side wall surface of the outer tubular member 18, and hence away from the sharpened interior edge 86 of the cutting port 84 during a cutting stroke. In previous types of instruments in which the distal edge surface of the inner cutting tube was formed with a single interior bevel to form the cutting edge, as illustrated for example in FIG. 15, there was a tendency for the inner tube to deflect slightly outwardly toward the edge of the cutting port as it moved forward into contact with the intraocular material being severed. This deflection was caused by the reaction force exerted by the material on the inside beveled surface of the cutting edge as the material became compressed between the cutting edge and the forward edge of the port. As a result of this deflection, the cutting edge of the inner tube would repeatedly strike the forward edge of the port, causing rapid dulling of the cutting edge. In addition, the repeated abrasion between the sharpened edge of the inner cutting tube and the edge of the cutting port also produced minute metal shavings which, if not removed by the aspiration system, would migrate into the vitreous body and remain there indefinitely. This result is less likely with the present invention due to the spacing provided between the cutting edge 96 of the inner tubular member and the sharpened edge 86 of the cutting port by virtue of the counter-bevel 94. The counter-bevel 94 also tends to induce a deflection of the inner tubular member 48 in a direction away from the sharpened edge 86 of the cutting port when intraocular material is compressed between the two edges, thereby cancelling the deflection that whould otherwise be caused by oppositely beveled portion 92 immediately above the cutting edge 96.

The counter-bevel 94 may be formed in any suitable manner, as by grinding the lower distal edge portion of the inner tubular 48 with a fine abrasive wheel. The counter-bevel 94 should extend at least around that portion of the distal edge of the inner tubular member 48 which overlaps that cutting port 84 during the cutting stroke. If desired, the counter-bevel 94 may be formed farther around the distal edge of the inner tubular member 48, to allow for some small degree of rotation of the inner tubular member 48 as the instrument operates. However, this is not necessary in cases where the actuating mechanism of the handpiece maintains the inner tubular member 48 in a fixed rotational position within the outer tubular member 18, as in the handpiece 10 of FIG. 1.

The manner in which the cutting instrument operates will be apparent from the sequential views of FIGS. 2 and 3. In FIG. 2, the inner tubular member 48 is in a retracted position behind the cutting port 84, this being the position if the inner tubular member when no pressure pulse is applied to the pneumatic actuator 30 of FIG. 1. Suction or aspiration is applied to the proximal end of the tubular member 48 through the flexible tube 22 of FIG. 1, resulting in intraocular tissue 98 being drawn in partially through the cutting port 84. A cutting stroke is initiated when a positive pressure pulse is applied to pneumatic actuator 30 within the handpiece, which produces a forward movement of the inner tubular member 48. This brings the cutting edge 96 of the inner tubular member into a shearing position with respect to the forward edge 86 of the cutting port 84, as shown in FIG. 3. This causes a small piece 100 of the tissue to be sheared off and removed by virtue of the suction or aspiration applied to the inner tubular member 48.

Upon completion of the cutting stroke, the inner tubular member 48 is moved back from the forward position illustrated in FIG. 3 to the retracted position of FIG. 2. This reverse movement is caused by the return spring 54 of FIG. 1 upon termination of the positive pressure pulse to the pneumatic actuator 30. Suction or aspiration may be applied to the inner tubular member 48 either continuously or intermittently, and in the latter situation it is advantageous to coordinate the application of suction with the cutting stroke of the surgical instrument. This may be accomplished by using the automatic aspiration system disclosed in the applicants' U.S. Pat. No. 4,324,243, which patent is expressly incorporated herein by reference.

It should be understood that the formation of a sharpened edge 86 on the inside surface of the cutting port 84, although desirable, is not essential to the practice of the present invention. Cutting is performed principally by the shearing action of the sharpened edge 96 of the moving inner tubular member 48 as it closes off the cutting port 84. Such cutting will occur regardless of whether the inner edge 84 of the port is sharpened, although the shearing will be more efficient if the sharpened edge 86 is provided.

FIGS. 8-10 are sectional views illustrating three different types of shapes which may be used for the tapered distal end of inner tubular member 48. In FIG. 8, the distal end 92 of the inner tubular member 48 is provided with a straight bevel, preferably at an angle of about 45°, as already shown in FIGS. 2-3. This is the preferred shape for the distal end of the inner tubular member 48 since it is the easiest to fabricate and provides a strong and durable tip. In FIG. 9, an alternative inner tubular member 48° is shown in which the distal end surface is provided with a concave bevel 92' having a curved profile. FIG. 10 illustrates yet another type of inner tubular member 48'', in which the tapered distal end portion is formed by removing a semicylindrical section from the end of the tube and then beveling the remaining portion to form a partial bevel 92'. The tip shapes shown in FIGS. 9 and 10 are equally capable of moving into the beveled distal portion of the outer tubular member 18 of FIGS. 2-3, but are somewhat more difficult to fabricate than the straight beveled tip of FIG. 8. All three embodiments are preferably provided with counter-bevels 94, 94' and 94'' along their distalmost edges, as described earlier, to provide cutting edges 96, 96' and 96'', respectively, which are spaced slightly away from the outer wall surfaces of the inner tubular members 48, 48' and 48''.

It should be apparent that, in addition to the particular configurations illustrated in FIGS. 8-10, the distal end of the inner tubular member 48 can have any shape which is asymmetrically tapered in a manner permitting at least some degree of nesting within the beveled distal end of the outer tubular member 18. The condition of asymmetry refers to the fact that the distal end of the inner tubular member 48, regardless of its specific configuration, will not be symmetric about a horizontal plane which includes the longitudinal axis of the inner tubular member and which is perpendicular to the axis of the side opening 84 of the outer tubular member 18 in FIGS. 2 and 3. It should also be apparent that, in the event that the distal end of the inner tubular member 48 is tapered other than by means of the straight bevel 92 of FIG. 8, the distal end of the outer tubular member 18 can be provided with a complimentary shape. However, the straight beveled distal end of the outer tubular member 18 which is shown in the drawings is by far the easiest to fabricate and will therefore be preferred in most situations.

FIGS. 11–13 are sequential views illustrating a preferred method of making the surgical instrument of FIGS. 2–7. The method illustrated produces an inner tubular member 48 with a straight beveled distal end 92 as illustrated in FIG. 8, although the method can be varied, if desired, to produce alternative configurations at the distal end of the inner tubular member, such as those illustrated in FIGS. 9 and 10.

In accordance with the preferred method, an instrument blank is provided which comprises a rigid outer tube 18 and a rigid inner tube 48, the latter being coaxially and slidably arranged within the outer tube 18. The inner and outer tubular members 48 and 18 may comprise suitable lengths of stainless steel hypodermic tubing, as described earlier. The inner and outer tubes 48 and 18 comprising the instrument blank each have open distal and proximal ends. With reference to FIG. 11, which shows the distal portions of the tubes 48 and 18, a hole 84 is formed in the side wall of the outer tubular member 18 at a point near its distal end. The hole 84 is preferably hollow ground using a fine cylindrical abrasive wheel, as described earlier. This process will produce an indentation 102, and in some cases a complete through-hole, in the side wall of the inner tubular member 48. The grinding process automatically produces a sharpened cutting edge along the inner surface of the opening 84 as noted previously. The formation of the indentation 102 on the inner tubular member 48 can be avoided, if desired, by retracting the inner tubular member to a point well behind the distal opening of the outer tubular member 18 before the opening 84 is formed. However, it is preferable to leave the inner tubular member 48 in the position shown in FIG. 11 since it provides support for the side walls of the outer tubular member 18 during formation of the opening 84.

After the side opening 84 has been formed, the inner tubular member is advanced so that its distal end, including the part containing the indentation 102, projects out of the distal end of the outer tubular member 18. An oblique cut is then formed simultaneously through the inner and outer tubular member 48 and 18 at a point between the distal end of the outer tube and the opening 84 which has already been formed in the side wall of the outer tube 18. The appearance of the instrument blank is now as shown in FIG. 12. The distal cut portions of the inner and outer tubes 48 and 18, illustrated on the right-hand side of FIG. 12, are not used in the final instrument and are discarded as waste.

At this point in the process, the inner and outer tubes 48 and 18 have been provided with the desired oblique cut ends, which are necessarily at the same angle since both tubes were cut during a single cutting operation. Prior to closing off the distal end of the outer tube 18, as will next be described in connection with FIG. 13, it is desirable to provide the distal end of the inner tube 48 with the counter-bevel 94 as illustrated earlier in FIG. 7. This may be done by advancing the inner tube 48 so that its oblique cut distal end projects out of the oblique cut distal end of the outer tube 18, and then shaping the distalmost edge of the inner tube 48 with an abrasive wheel to form the counter-bevel 94. It is also possible to form the counter-bevel 94 after the outer tube 18 has been closed off, although this requires complete removal of the inner tube 48 from the proximal end of the outer tube 18, followed by reinsertion of the inner tube into the outer tube. Since both tubes have very small gauges, the reinsertion step can prove quite difficult if done manually. For this reason, it is preferable to form the counter-bevel 94 prior to closing the outer tube 18 as described previously.

With reference now to FIG. 13, the instrument is completed by closing off the oblique cut distal end of the outer tube 18 to provide a closed instrument tip. This is accomplished by withdrawing the inner tube 48 to a position well behind the distal opening of the outer tube 18, as shown, and then inserting a flat elliptical disk or plug 82 into the end of the outer tube 18 in a flush position. The disk or plug 82 is then securely joined to the inner side walls of the outer tube 18. Although the disk or plug 82 can be made of any suitable material, such as metal or plastic, a metal such as stainless steel is preferred since this allows the disk or plug to be firmly secured within the end of the outer tube 18 by a welding process. Once in place, the disk or plug 82 forms an inclined end wall for the outer tube 18 as shown in FIGS. 2 and 3. The upper distal edge of the outer tube 18 may then be rounded off by grinding or the like to produce the rounded surface 88 of FIGS. 2 and 3.

It should be noted that the oblique cut formed through the inner and outer tubes 48 and 18, as illustrated in FIG. 12, inherently produces a sharpened edge at the distal end of the inner tube 48. This edge may be left intact, if desired, and used as the cutting edge of the inner tubular member 48 in the completed instrument. However, for the reasons given previously, it is preferable to form the counter-bevel 94 which effectively spaces the cutting edge away from the interior side wall surface of the outer tube 18, and hence away from the interior edge of the cutting port 84 during the cutting stroke.

Following the completion of the distal portion of the instrument as described above, appropriate finishing steps may be performed to adapt the instrument to the powered handpiece 10 of FIG. 1. Such finishing steps would include, for example, cutting the outer tube 18 to a length shorter than the length of the outer tube 18. This allows the proximal end of the inner tube 48 to project sufficiently beyond the proximal end of the outer tube 18 so that the inner tube 48 can be connected to the flexible suction or aspiration line 22. Another finishing step would involve the press-fitting of the platform member 44 to the inner tube 48 at a point near the proximal end of the inner tube, as illustrated in FIG. 1. Alternatively, this may be done indirectly by press-fitting the platform member 44 to a short length of tubing (not shown) which has the same gauge as the outer tube 18. The short section of tubing, with the platform member affixed thereon, is then slipped over the proximal end of the inner tube 48. With the proximal part of the outer tube 18 firmly held by the anterior section 12 of the handpiece housing as illustrated in FIG. 1, the inner tube 48 is moved forward to its desired distalmost position just beyond the cutting port 84. With the platform member 44 held against the annular shoulder 60 of FIG. 1, the short section of tubing on which the platform member 44 is mounted may now be welded or brazed to the inner tube 48. The flexible suction or aspiration tube 22 may then be attached to the part of the short section of tubing which overlaps the proximal end of the inner tube 48. This method provides a convenient way of securing the platform member 44 to the inner tubular member 48 while at the same time insuring that the platform member occupies the exact position on the inner tubular member 48 to produce the desired stroke of movement at the cutting tip.

FIG. 14 is a sectional view of the human eye illustrating the manner in which the vitrectomy instrument of the present invention may be used to remove unwanted intraocular material near the retina. For clarity, the handpiece 10 of FIG. 1 has been omitted from FIG. 14 and only the instrument portion 17 is shown. In accordance with conventional practice, an incision is made in the pars plana region 104 of the eye between the anteriormost part of the retina 106 and the ciliary body 108. The instrument 17 is inserted through this incision and the cutting port 84 is positioned in proximity to the material to be cut. Such material might comprise, for example, fibrous scar tissue resulting from intraocular hemorrhage or spontaneously formed epiretinal membranes. The cutting procedure is visualized by the surgeon through the cornea 110 and dilated pupil within the iris 112, using a high-powered operating microscope.

Figure 16:
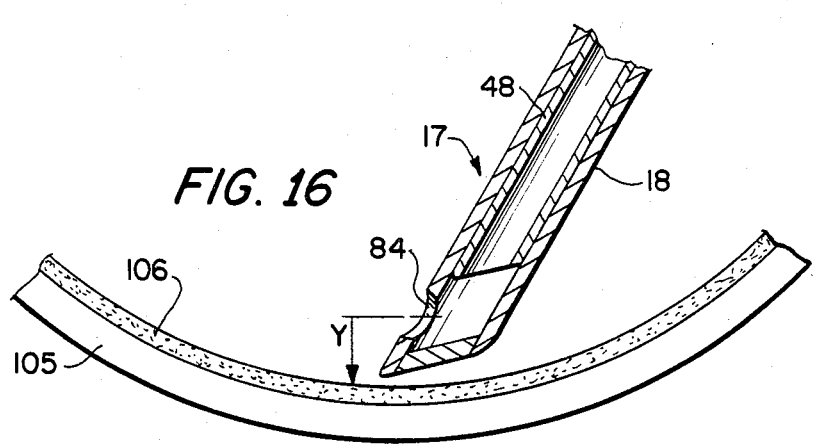
FIG. 16 is a detailed sectional view of the human eye illustrating the vitrectomy instrument of the present invention in position for cutting intraocular material near the retina.

FIGS. 15 and 16 illustrate the manner in which the present invention may be used to excise material located much closer to the retinal surface than would be possible using a typical prior art instrument. FIG. 15 illustrates one such prior art instrument, in which the distal tip 114 of the outer tube 116 is hemispherical in shape. Since the sharpened distal end of the vertical cut inner tube 118 cannot move into the rounded distal tip of the instrument, the cutting port 120 is required to be positioned rather relatively far from the instrument tip. When the instrument is positioned close to the retina 106, as illustrated in FIG. 15, there is a relatively large distance between the cutting port 120 and the retinal surface. This distance is represented by the arrow labelled x in FIG. 15. In order to cut material located very close to the retina using this instrument, it is typically necessary to employ a second instrument in order to elevate the material to the level of the cutting port 120. It should be noted that any attempt by the surgeon to manipulate the instrument to bring the cutting port closer to the retina 106, as by rotating the outer tube 118 through an angle of 180° or reversing the angle of the instrument, will obscure the cutting port 120 from view and will therefore make the surgery difficult and hazardous.

Referring now to FIG. 16, in which the surgical instrument 17 of the present invention is shown in position near the retina, it is readily seen that the distance y between the cutting port 84 and the surface of the retina 106 is much smaller. This allows cutting of intraocular material much closer to the retina 106 than would be possible using the prior art instrument of FIG. 15. The beveled distal end surface of the outer tubular member 18 in the present invention more nearly follows the contour of the retinal surface than does the symmetrically rounded instrument tip 114 of FIG. 15. When the instrument tip of the present invention is positioned so that its beveled end surface lies along the retina, as illustrated in FIG. 16, the cutting port is positioned close to the retina and is located in a direct line of sight with the anterior part of the eye. Thus the asymmetrical shape of the instrument tip in FIG. 16, in addition to enabling the port 84 to be positioned very close to the instrument tip as described earlier, also performs the useful function of allowing the instrument tip to lie almost flush against the retina without obscuring the cutting port 84. In practice, the surgeon may prefer to employ a variety of different instrument tips of the type illustrated in FIG. 16, each with a different bevel angle at its distal end to enable material to be removed at different points along the circumference of the retina 106.

Figure 17:
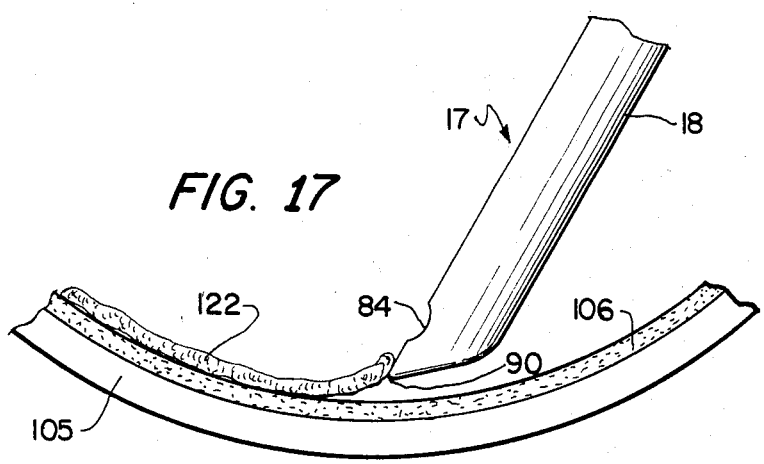
FIG. 17 is a detailed sectional view of the human eye illustrating the manner in which the instrument tip of the present invention may be used to elevate and dissect intraocular material prior to cutting.

FIG. 17 illustrates a commonly occurring situation in which the material to be excised is a thin epiretinal membrane 122. The membrane 122 is in contact with the retina 106 and cannot be excised until it is elevated far enough to be reached by the cutting port of the vitrectomy instrument. With previous types of vitrectomy instruments, this often required the use of a separate instrument, such as a hooked needle, for removing the membrane from the retina prior to cutting. With the present invention, however, this maneuver can be accomplished using the vitrectomy instrument 17 alone. As shown in FIG. 17, the beveled end of the outer tubular member 18 terminates in an edge surface 90 which can conveniently be used as a spatula for elevating the membrane 122 to a position where it can be drawn into the cutting port 84. This maneuver would be difficult or impossible with the symmetrically rounded tip of the prior art instrument shown in FIG. 15.

Although the present invention has been described with reference to a preferred embodiment, the scope of the invention is not limited to the details thereof. Various substitutions and modifications have been suggested in the foregoing description, and others will occur to those of ordinary skill in the art. All such substitutions and modifications are intended to be embraced within the scope of the appended claims.

What is claimed is:

1. An ophthalmic surgical instrument comprising rigid coaxial inner and outer tubular members with the inner tubular member axially slidable within the outer tubular member and in substantially continuous contact with the inside walls thereof, said outer tubular member having a closed distal end which is beveled at an oblique angle with respect to the longitudinal axis of the outer tubular member, said inner tubular member having an open distal end which is beveled at an oblique angle with respect to the longitudinal axis of the inner tubular member and which is movable into the beveled end of the outer tubular member, and said outer tubular member being provided with a distal side wall opening which occupies at least part of the non-beveled area opposite the beveled portion of the outer tubular member, wherein the portion of the distal edge surface of said inner tubular member which moves across the distal side wall opening in the outer tubular member is counter-beveled to provide a sharpened cutting edge which is spaced away from the edge of the distal side opening lying along the inside surface of the outer tubular member.

2. An ophthalmic surgical instrument as claimed in claim 1, wherein the oblique angle defined between the beveled end of the inner tubular member and the longitudinal axis of the inner tubular member is substantially equal to the oblique angle defined between the beveled end of the outer tubular member and the longitudinal axis of the outer tubular member.

3. An ophthalmic surgical instrument as claimed in claim 2, wherein said counter-bevel is formed at an angle of about 45° with respect to the longitudinal axis of the inner tubular member.

4. An ophthalmic surgical instrument as claimed in claim 2, wherein said inner and outer tubular members are circular in cross-section, and wherein the beveled distal end of the outer tubular member is closed by a flat elliptical disk joined to the side walls of the outer tubular member.

5. An ophthalmic surgical instrument as claimed in claim 4, wherein the distal ends of said inner and outer tubular members are each beveled at an angle of about 45° with respect to their respective longitudinal axes.

6. An ophthalmic surgical instrument as claimed in claim 4, wherein the side opening in the outer tubular member is elliptical in shape and has its major axis parallel to the longitudinal axis of the outer tubular member.

7. An ophthalmic surgical instrument as claimed in claim 6, wherein at least a portion the edge of said side opening which lies along the inside surface of the outer tubular member is sharpened to provide a second cutting edge.

8. An ophthalmic surgical instrument comprising:
(a) an elongated rigid outer tubular member having a circular cross-section with a constant inside diameter, said outer tubular member having its distal end beveled at an oblique angle with respect to the longitudinal axis of said outer tubular member, said distal end being closed by an inclined end wall joined to the side walls of said outer tubular member;
(b) an elongated rigid inner tubular member having a circular cross-section with a constant outside diameter, said inner tubular member being slidably and coaxially received within said outer tubular member and having an open distal end which is beveled at an oblique angle with respect to the longitudinal axis of the inner tubular member, said last-mentioned oblique angle being substantially equal to the oblique angle defined between the beveled distal end of the outer tubular member and the longitudinal axis of the outer tubular member;
(c) said inner tubular member being arranged for reciprocating forward and reverse movement within said outer tubular member along the longitudinal axis of the outer tubular member, with the forward movement of the inner tubular member carrying substantially the entire beveled distal end thereof into the beveled distal end of the outer tubular member and into close proximity to said inclined end wall;
(d) said outer tubular member being provided with a side opening in close proximity to its distal end, said opening occupying at least part of the non-beveled side wall area of the outer tubular member that is opposite the inclined end wall; and
(e) said inner tubular member having a counter-beveled cutting edge along the portion of its open distal end which sweeps past the side opening in the outer tubular member during the forward and reverse movement of the inner tubular member, said counter-bevel providing a sharpened cutting edge which is spaced away from the edge of the distal side opening lying along the inside surface of the outer tubular member.

9. An ophthalmic surgical instrument as claimed in claim 4, wherein said inclined end wall comprises a flat elliptical disk joined to the side walls of the outer tubular member at the beveled distal end thereof.

10. An ophthalmic surgical instrument as claimed in claim 9, wherein the oblique angle defined between the beveled distal end of the outer tubular member and the longitudinal axis of the outer tubular member, and the oblique angle defined between the beveled distal end of the inner tubular member and the longitudinal axis of the inner tubular member, are both about 45°.

11. An ophthalmic surgical instrument as claimed in claim 10, wherein said counter-bevel is formed at an angle of about 45° with respect to the longitudinal axis of the inner tubular member.

12. An ophthalmic surgical instrument as claimed in claim 9, wherein the side opening in said outer tubular member is elliptical in shape and has its major axis parallel to the longitudinal axis of the outer tubular member.

13. An ophthalmic surgical instrument as claimed in claim 12, wherein at least a portion of the edge of said side opening which lies along the inside surface of the outer tubular member is sharpened to provide a second cutting edge.

14. In an ophthalmic surgical apparatus comprising a handpiece portion and a projecting instrument portion, said instrument portion comprising rigid coaxial inner and outer tubular members with the inner tubular member axially slidable within the outer tubular member, and said handpiece portion comprising power-operated means for axially reciprocating said inner tubular member within said outer tubular member to produce a desired cutting function at the instrument tip, the improved instrument portion comprising an outer tubular member having a closed and beveled distal end, an inner tubular member having an open distal end which is similarly beveled and which is movable into the beveled end of the outer tubular member, said outer tubular member being provided with a distal side wall opening which occupies at least part of the non-beveled area opposite the beveled portion of the outer tubular member, and said inner tubular member being in substantially continuous contact with the inside walls of the outer tubular member and having a counter-beveled cutting edge at its open distal end.

15. An ophthalmic surgical apparatus as claimed in claim 14, wherein said counter-bevel is formed at an angle of about 45° with respect to the longitudinal axis of the inner tubular member.

16. An ophthalmic surgical apparatus as claimed in claim 14, wherein said inner and outer tubular members are circular in cross-section, and wherein the beveled distal end of the outer tubular member is closed by a flat elliptical disk joined to the side walls of the outer tubular member.

17. An ophthalmic surgical apparatus as claimed in claim 16, wherein the distal ends of said inner and outer tubular members are each beveled at an angle of about 45° with respect to their respective longitudinal axes.

18. An ophthalmic surgical apparatus as claimed in claim 17, wherein the side opening in the outer tubular member is elliptical in shape and has its major axis parallel to the longitudinal axis of the outer tubular member.

19. An ophthalmic surgical apparatus as claimed in claim 18, wherein at least a portion of the edge of said opening which lies along the inside surface of the outer tubular member is sharpened to provide a second cutting edge.

* * * * *